United States Patent
Inenaga et al.

(10) Patent No.: US 11,332,694 B2
(45) Date of Patent: May 17, 2022

(54) PYRROLE COMPOUND, METHOD OF MAKING SAME, AND AROMA COMPOSITION, FOOD, DRINK AND COSMETICS CONTAINING SAME

(71) Applicant: T. HASEGAWA CO., LTD., Tokyo (JP)

(72) Inventors: Shunsuke Inenaga, Kawasaki (JP); Keisuke Yoshikawa, Kawasaki (JP); Yamato Miyazawa, Kawasaki (JP); Makiko Ito, Kawasaki (JP)

(73) Assignee: T. HASEGAWA CO., LTD., Tokyo (JP)

( * ) Notice: Subject to any disclaimer, the term of this patent is extended or adjusted under 35 U.S.C. 154(b) by 195 days.

(21) Appl. No.: 16/630,645

(22) PCT Filed: May 23, 2018

(86) PCT No.: PCT/JP2018/019862
§ 371 (c)(1),
(2) Date: Jan. 13, 2020

(87) PCT Pub. No.: WO2019/021608
PCT Pub. Date: Jan. 31, 2019

(65) Prior Publication Data
US 2020/0157463 A1 May 21, 2020

(30) Foreign Application Priority Data
Jul. 26, 2017 (JP) .............................. JP2017-144630

(51) Int. Cl.
| | |
|---|---|
| *C11B 9/00* | (2006.01) |
| *C07D 207/335* | (2006.01) |
| *C07D 207/333* | (2006.01) |
| *A61K 8/49* | (2006.01) |
| *A61Q 13/00* | (2006.01) |
| *A23F 3/40* | (2006.01) |
| *A23F 3/16* | (2006.01) |
| *A23F 5/46* | (2006.01) |
| *A23F 5/24* | (2006.01) |
| *A23L 2/56* | (2006.01) |
| *A23L 27/27* | (2016.01) |
| *A23L 27/20* | (2016.01) |
| *C12C 5/02* | (2006.01) |

(52) U.S. Cl.
CPC .............. *C11B 9/0092* (2013.01); *A23F 3/16* (2013.01); *A23F 3/405* (2013.01); *A23F 5/24* (2013.01); *A23F 5/465* (2013.01); *A23L 2/56* (2013.01); *A23L 27/2054* (2016.08); *A23L 27/27* (2016.08); *A61K 8/4913* (2013.01); *A61Q 13/00* (2013.01); *C07D 207/333* (2013.01); *C07D 207/335* (2013.01); *C12C 5/026* (2013.01); *A23V 2002/00* (2013.01)

(58) Field of Classification Search
CPC ........ A23L 27/2065; A23L 27/27; A23L 2/56; C11B 9/0092; A23F 3/16; A23F 3/405; A23F 5/24; A23F 5/465; A61K 8/4913; A61Q 13/00; C07D 207/333; C07D 207/335; C12C 5/026; A23V 2002/00
See application file for complete search history.

(56) References Cited

U.S. PATENT DOCUMENTS

| 3,869,554 A | 3/1975 | Pittet et al. | |
|---|---|---|---|
| 2003/0152601 A1* | 8/2003 | Kanayama | ............. A61K 8/922 424/401 |

FOREIGN PATENT DOCUMENTS

| JP | S49-14668 A | 2/1974 |
|---|---|---|
| JP | H55-76813 A | 6/1980 |
| JP | H08-113560 A | 5/1996 |
| JP | 2005143467 A | 6/2005 |
| JP | 2010207116 A | 9/2010 |
| JP | 2015208286 A | 11/2015 |
| WO | WO2017064635 | * 4/2017 |

OTHER PUBLICATIONS

International Search Report (PCT/ISA/210) dated Jul. 3, 2018, by the Japanese Patent Office as the International Searching Authority for International Application No. PCT/JP2018/019862.
Written Opinion (PCT/ISA/237) dated Jul. 3, 2018, by the Japanese Patent Office as the International Searching Authority for International Application No. PCT/JP2018/019862.
Amarnath, V., et al., "The mechanism of nucleophilic substitution of alkylpyrroles in the presence of oxygen", Chemical Research in Toxicology, 1994, vol. 7, No. 1, pp. 56-61.
Hara, T., et al., "Changes in aroma components of green tea during the firing process", Nippon Nogei Kagaku Kaishi, 1984, vol. 58, No. 1, pp. 25-30.

(Continued)

*Primary Examiner* — Anthony J Weier
(74) *Attorney, Agent, or Firm* — Buchanan Ingersoll & Rooney PC

(57) ABSTRACT

A compound represented by the following formula (1):

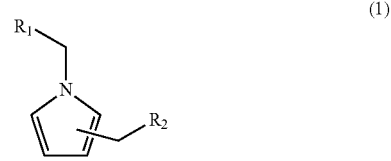

wherein, $R_1$ is a linear or branched alkyl group having 1 to 3 carbon atoms or a hydroxyl group; and $R_2$ is a 1-pyrrolyl group, a 2-pyrrolyl group, or a 3-pyrrolyl group. The present invention can provide a means highly effective in contributing to savory roasting flavor and capable of imparting fragrance with natural feeling.

14 Claims, No Drawings

(56) References Cited

OTHER PUBLICATIONS

Mizukami, Y., et al., "Changes in the concentrations of acrylamide, selected odorants, and catechins caused by roasting of green tea", Journal of Agricultural and Food Chemistry, 2008, vol. 56, No. 6, pp. 2154-2159.

Mizukami, Yuzo, "Identification of key odorants in roasted green tea by using solvent-assisted flavor evaporation apparatus under high vacuum and application of the aroma extract dilution analysis", Tea Research Journal, 2012, No. 113, pp. 55-62.

* cited by examiner

PYRROLE COMPOUND, METHOD OF MAKING SAME, AND AROMA COMPOSITION, FOOD, DRINK AND COSMETICS CONTAINING SAME

TECHNICAL FIELD

The present invention relates to a pyrrole compound, an aroma composition, and a food and drink and a cosmetics containing the same.

BACKGROUND ART

Aroma and taste of food and drink having great influence on preference of consumers are considered as one of important factors that characterize the food and drink. In recent years, food and drink with various kinds of fragrance and flavor have been demanded with diversification of preference of consumers. Further, aroma is an important factor not only in food and drink, but also in the field of cosmetics. There is a growing need for products having fragrance and flavor with natural feeling with an increasing demand for high-end products.

Under such circumstances, an aroma component of food and drink and cosmetics is added as an aroma ingredient as a technique for enhancing or imparting desired flavor and fragrance.

In particular, food and drink and cosmetics to which savory roasting fragrance and flavor found in roasted food and drink are imparted are extremely highly preferred and considered as one of products which are expected to be in increasing demand for times to come.

For example, JP 2015-208286 A proposes a technique for adding roasted tea extract including various pyrazine-based compounds such as 2-methylpyrazine for the purpose of imparting natural roasting aroma to food and drink. Further, examples of a compound capable of imparting such roasting aroma include 2-ethyl-3,5-dimethylpyrazine, 2-vinyl-3,5-dimethylpyrazine, guaiacol, and the like (Yuzo Mizukami: Identification of key odorants in roasted green tea by using solvent-assisted flavor evaporation apparatus under high vacuum and application of the aroma extract dilution analysis. Tea Research Journal (2012), No. 113, 55-62).

SUMMARY OF INVENTION

However, there has been a demand for a means capable of easily obtaining savorier roasting flavor and imparting aroma excellent in natural feeling.

Thus, the present invention has been made in view of the above circumstances, and an object of the present invention is to provide a means highly effective in contributing to savory roasting flavor and capable of imparting fragrance with natural feeling.

As a result of conducting extensive studies to solve the aforementioned problems, the present inventors have found that a pyrrole analogous compound represented by the following formula (1) easily contributes to savory roasting flavor and has aroma with natural feeling, thereby completing the present invention.

Specifically, the above object can be achieved by the following means.

1. A compound represented by the following formula (1):

[Chemical Formula 1]

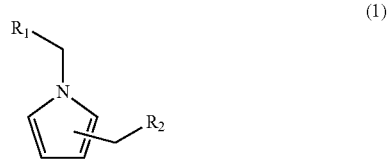

[wherein, $R_1$ is a linear or branched alkyl group having 1 to 3 carbon atoms or a hydroxyl group; and $R_2$ is a 1-pyrrolyl group, a 2-pyrrolyl group, or a 3-pyrrolyl group.]

2. An aroma composition including a compound represented by the following formula (1) as an active ingredient.

3. A food and drink including the compound according to 1. or the aroma composition according to 2;

4. The food and drink according to 3. being a tea beverage.

5. A cosmetics including the compound according to 1. or the aroma composition according to 2.

6. A method for imparting roasting aroma to a food and drink, including a step of adding the compound according to 1. or the aroma composition according to 2. to the food and drink.

DESCRIPTION OF EMBODIMENTS

Hereinafter, embodiments of the present invention are described.

[Pyrrole Compound]

An embodiment of the present invention is a compound represented by the following formula (1):

[Chemical Formula 2]

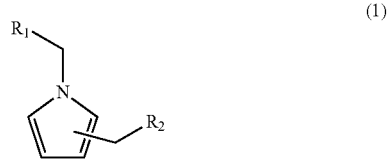

[wherein, $R_1$ is a linear or branched alkyl group having 1 to 3 carbon atoms or a hydroxyl group; and $R_2$ is a 1-pyrrolyl group, a 2-pyrrolyl group, or a 3-pyrrolyl group.]

The present inventors have surprisingly found that a pyrrole compound having two pyrrole rings (sometimes also simply referred to as "compound according to one embodiment of the present invention", "pyrrole compound", etc. in the present description) represented by the above formula (1), which is different from a pyrazine-based compound or the like conventionally known as a compound contributing to roasting aroma, easily contributes to savory roasting flavor (highly contributes to aroma) and has an odor with natural feeling. Thus, adding the pyrrole compound represented by the above formula (1) to food and drink and cosmetics can impart excellent roasting aroma with natural feeling to these products. Thus, according to the present invention, there is provided a means highly effective in contributing to savory roasting flavor and capable of imparting aroma with natural feeling.

Hereinafter, the pyrrole compound according to one embodiment of the present invention will be described.

In the above formula (1), $R_1$ is a linear or branched alkyl group having 1 to 3 carbon atoms or a hydroxyl group (—OH group). Specific examples of the linear or branched alkyl group having 1 to 3 carbon atoms as $R_1$ include a methyl group, an ethyl group, an n-propyl group, and an isopropyl group.

Of these, an alkyl group with a small number of carbon atoms and a hydroxyl group are preferable from the viewpoint of obtaining a compound having a higher contribution to aroma (capable of exhibiting roasting aroma in a small amount). Specifically, $R_1$ is preferably a methyl group, an ethyl group, or a hydroxyl group (—OH group), more preferably a methyl group or a hydroxyl group, particularly preferably a methyl group.

In the above formula (1), $R_2$ is a 1-pyrrolyl group (following formula (a)), a 2-pyrrolyl group (following formula (b)), or a 3-pyrrolyl group (following formula (c)) (note that "*" in the following formulae (a) to (c) represents a binding site).

[Chemical Formula 3]

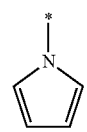
(a)

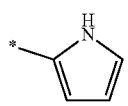
(b)

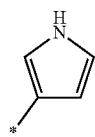
(c)

Of these, $R_2$ is preferably a 1-pyrrolyl group (above formula (a)) or a 2-pyrrolyl group (above formula (b)), particularly preferably a 1-pyrrolyl group (above formula (a)), from the viewpoint of achieving a simple production step and obtaining a compound having a higher contribution to aroma (capable of exhibiting roasting aroma in a small amount). If $R_2$ is a 1-pyrrolyl group, the polarity of the compound becomes relatively low as compared with a case where $R_2$ is a 2-pyrrolyl group or a 3-pyrrolyl group, resulting in a reduction in the melting point and boiling point, which presumably leads to a further higher contribution to fragrance.

Further, in the above formula (1), a substitution position of "—$CH_2$—$R_2$" on the pyrrole ring may be the 2-position (following formula (1-1)) or the 3-position (following formula (1-2)). That is, the compound represented by the above formula (1) can take the following forms:

[Chemical Formula 4]

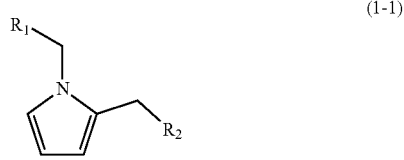
(1-1)

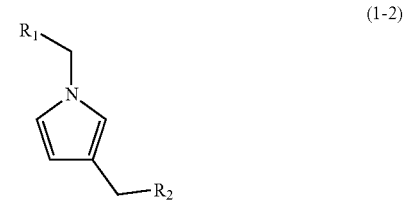
(1-2)

Of these, the substitution position of "—$CH_2$—$R_2$" on the pyrrole ring is preferably the 2-position (above formula (1-1)) from the viewpoint of obtaining a compound having a high contribution to aroma.

Preferable examples of the compound represented by the above formula (1) include the following compounds (A) to (E). Of these, the compounds (A) and (B) are preferable from the viewpoint of having a high contribution to aroma.

[Chemical Formula 5]

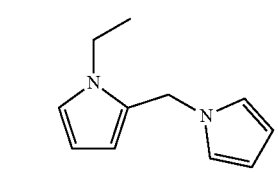
(A)

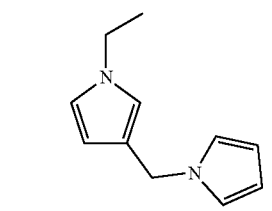
(B)

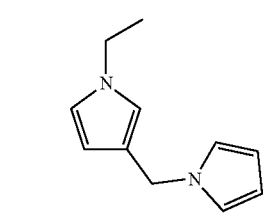
(C)

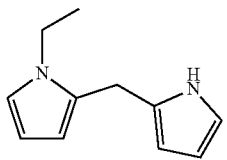
(D)

(E)

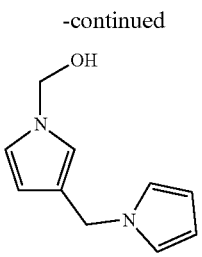

A method for producing the above pyrrole compound is not particularly limited. The pyrrole compound may be synthesized or extracted from a natural product (e.g., coffee, green tea, black tea, oolong tea, barley tea, etc.).

The above pyrrole compound can be synthesized by appropriately modifying known methods or combining them. For example, the above pyrrole compound can be synthesized by simultaneously performing the Appel reaction and an addition reaction using 1-alkylpyrrole and 1-hydroxymethyl pyrrole (e.g., see the reaction formula (2) in the section of Examples). Further, a method in which a hydroxyl group of 1-hydroxymethyl pyrrole is halogenated by a known method to obtain a halide and then the halide is subjected to a coupling reaction with 1-alkylpyrrole may be used. Further, a method of performing a coupling reaction between 1-alkyl-2-hydroxymethyl pyrrole and pyrrole (e.g., see the reaction formula (5) in the section of Examples) may be used.

An extraction method from a natural product is also not particularly limited. The above pyrrole compound can be obtained by performing extraction using an appropriate solvent, followed by concentration.

[Aroma Composition]

The present invention also provides, in another embodiment, an aroma composition including the above pyrrole compound. That is, another embodiment of the present invention is an aroma composition including a compound represented by the following formula (1) as an active ingredient:

[Chemical Formula 6]

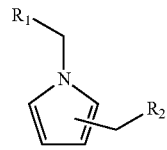

(1)

[Wherein, $R_1$ is a linear or branched alkyl group having 1 to 3 carbon atoms or a hydroxyl group; and $R_2$ is a 1-pyrrolyl group, a 2-pyrrolyl group, or a 3-pyrrolyl group.]

As described above, the compound represented by the above formula (1) contributes to savory roasting flavor and has fragrance with natural feeling. Thus, adding the aroma composition including the compound represented by the above formula (1) to food and drink and cosmetics can impart excellent roasting aroma with natural feeling to these products. Note that the above pyrrole compound included in the aroma composition may be used singly, or two or more thereof may be used by mixing.

The aroma composition according to the present embodiment includes the above pyrrole compound as an active ingredient. In this description, the above pyrrole compound being "included as an active ingredient" means that the above pyrrole compound is included in an amount for sufficiently exhibiting desired aroma (roasting aroma). Thus, while the aroma composition according to the present embodiment may include only the pyrrole compound according to the present invention, the aroma composition may also include other aroma components, other additives such as a solvent, and the like as long as desired aroma is not impaired.

Other aroma components are not particularly limited, and a known aroma component can be used. Examples thereof include various kinds of synthetic perfume, natural perfume, natural essential oil, plant extract, and the like. Examples thereof include natural essential oil, natural perfume, and synthetic perfume described in "Japan Patent Office, Collection of Well-Known Prior Arts (Flavor or Fragrance), Part II Food Flavor or Fragrance, P7-87, published on Jan. 14, 2000)".

Examples of such aroma compound include a hydrocarbon such as ocimene, limonene, β-caryophyllene, α-farnesene, α- or β-pinene, α, β- or γ-terpinene, camphene, α-cedrene, myrcene, α- or β-phellandrene, p-cymene, α- or β-cadinene, 1- or 2-methylnaphthalene, 1-isopropyl-4-methylbenzene, 1,4-dimethylbenzene, ethylbenzene, trimethylbenzene, ethylmethylbenzene, propylbenzene, isopropylbenzene, dimethylstyrene, t-butylbenzene, diethylbenzene, methylpropylbenzene, tetrahydronaphthalene, 1,1-dimethylnaphthalene, trimethyldihydronaphthalene, 1,6-dimethyl-4-methylnaphthalene, 3-methyl-6-(1-methylethylidene)cyclohexene, and δ-3-carene; an alcohol such as n-propanol, 2-propanol, n-butanol, isobutyl alcohol, 2-butanol, 2-pentanol, 3-pentanol, 2-methyl-3-butene-2-ol, isoamyl alcohol, amyl alcohol, n-hexanol, (Z)-2-pentene-1-ol, 1-pentene-3-ol, (E)-2-hexene-1-ol, (Z)- or (E)-3-hexene-1-ol, 2-ethyl-1-hexanol, heptanol, octanol, 2-octene-1-ol, 1-octene-3-ol, 1,5-octadiene-3-ol, n-nonanol, benzyl alcohol, 2-phenoxyethanol, 1- or 2-phenylethyl alcohol, phenylethyldimethylcarbinol, 2,4-dimethoxybenzenemethanol, hydroxycitronellal, citronellol, geraniol, nerol, linalool, farnesol, nerolidol, α-terpineol, 1- or 4-terpineol, α- or 5-cadinol, cubenol, β-eudesmol, cedrol, carveol, myrtenol, isophytol, 3,7-dimethyl-1,5,7-octatriene-3-ol, 3,7-dimethyl-1,5-octadiene-3,7-diol, menthol, 4-penten-1-ol, 2-methylbutane-1-ol, 1-hexene-3-ol, 2-methyl-1-pentene-3-ol, 2-methyl-2-pentanol, 3-methyl-2-pentanol, (E)-4-heptenol, 2-methylhexanol, 2,5-octadienol, (E,E)-3,5-octadiene-3-ol, (E)-2-octenol, 5-undecanol, p-mentha-1,4-diene-7-ol, 4-terpinol, 1-terpineol, borneol, dihydrocarveol, E,E-farnesol, and phytol; an aldehyde such as acetaldehyde, propanal, isobutanal, butanal, valeraldehyde, isovaleraldehyde, (E)-2-heptenal, (Z)-4-heptenal, (E)-2-pentenal, (Z)-3-pentenal, 2-methylbutanal, hexanal, (E)-2-hexenal, (Z)-3-hexenal, (E,E)-2,4-hexadienal, (E,Z)-2,4-hexadienal, heptanal, (E,Z)-2,4-heptadienal, (E,E)-2,4-heptadienal, octanal, (E)-2-octenal, (E,E)-2,4-octadienal, (E,Z)-2,4-octadienal, nonanal, (E)-2-nonenal, (E,E)- or (E,Z)-2,4-nonadienal, (E,Z)-2,6-nonadienal, decanal, (E)-2-decenal, (E)-4,5-epoxy-2-decenal, (E,E)-2,4-decadienal, (E)-2-undecanal, salicylaldehyde, p-hydroxybenzaldehyde, 2,5-dimethylbenzaldehyde, vanillin, perillaldehyde, cinnamaldehyde, hexyl cinnamaldehyde, safranal, geranial, neral, β-cyclocitral, anisaldehyde, benzaldehyde, 2-phenylbutanal, 2-methyl-2-pentenal, 4-methyl-2-pentenal, 2-methylpentanal, 3-methylpentanal, 2,4-dimethyl-2,4-heptadienal, 2,4,6-decatrienal, (E)-2-tridecenal, 4-ethyl-7,11-dimethyl-(2E,6,10E)-dodecatrienal, benzaldehyde, 2- or 4-methylbenzaldehyde, 4-ethylbenzaldehyde, 4-hydroxy-3, 5-dimethoxybenzaldehyde, 4-methyl-2-phenyl-2-pentenal, and 5-methyl-2-phenyl-2-hexanal.

A ketone such as ethyl methyl ketone, acetoin, diacetyl, (Z)- or (E)-3-penten-2-one, 4-methyl-3-penten-2-one, 3-hexene-2-one, 2-heptanone, 3,5-heptadiene-2-one, 6-methyl-3,5-heptadiene-2-one, 1-octene-3-one, 3-octene-2-one, 4-octene-2-one, (E,Z), (E,E)-, or (Z,E)-3,5-octadiene-2-one, (Z)-1,5-octadiene-3-one, 3-methyl-2,4-nonanedione, 2-decanone, 2,6,10-trimethylheptadecanone, cyclohexanone, cis-jasmon, 2,2,6-trimethylcyclohexanone, α- or β-damascenone, α- or β-damascone, 4-oxo-β-ionone, α- or β-ionone, 5,6-epoxy-β-ionone, 3,4-dihydro-β-ionone, 7,8-dihydro-α-ionone, 5,6-dihydroxy-β-ionone, geranylacetone, 2,3-pentanedione, 2-pentanone, 3-pentanone, 4-methyl-3-pentene-2-one, 2-heptanone, (3E,5E)-6-methylheptadiene-2-one, 2-methyl-2-heptene-6-one, 2-octanone, 3-octanone, 2-nonanone, 5-ethyl-6-methyl-2-heptanone, 2-decanone, 6,10-dimethyl-2-undecanone, methyltetradecane-3-one, 6,10,14-trimethyl-2-pentadecanone, 2,3-dimethylcyclohexanone, 3-hydroxycyclohexanone, isophorone, 2,6,6-trimethylcyclohexanone, 2,2,6-trimethyl-6-hydroxycyclohexanone, 2,2,6-trimethyl-4-hydroxycyclohexanone, 2-hydroxyacetophenone, 4-methylacetophenone, 1,3- or 1,4-diacetylbenzene, 4-ethylacetophenone, 3,4-dimethylacetophenone, benzyl ethyl ketone, 2-methoxymethylacetophenone, 1-(2,4-dimethoxyphenyl)-1-propanone, camphor, fenchone, pulegone, 4-(1-hydroxy-4-oxo-2,6,6-trimethyl-2-cyclohexenyl)-3-butene-2-one, 1,5,5,9-tetramethylbicyclo-[4.3.0]-8-nonene-7-one, and 1,2-threo-1,2-dihydroxy-β-ionone; a carboxylic acid such as acetic acid, propionic acid, pentanoic acid, 4-methylpentanoic acid, (E)-2-hexenoic acid, (Z)-3-hexenoic acid, heptanoic acid, octanoic acid, nonanoic acid, decanoic acid, decenoic acid, (E)-2-decenoic acid, (Z)- or (E)-geranic acid, citronellic acid, benzoic acid, phenylacetic acid, salicylic acid, formic acid, 2-oxobutyric acid, 2-hydroxybutyric acid, 3-methyl-2-butenoic acid, 2- or 3-methylbutanoic acid, Z-2-hexenoic acid, E-3-hexenoic acid, 4-methyl-4-heptenoic acid, 2,3- or 4-methylpentanoic acid, hexanoic acid, (2E,4Z)- or (E,4E)-heptadienoic acid, Z-2-heptenoic acid, (Z)- or (E)-4-heptenoic acid, 2,3- or 5-methylhexanoic acid, (E)-2-octenoic acid, (Z)-3- or 4-octenoic acid, 2-ethylhexanoic acid, 2,3- or 6-methylpentanoic acid, (E)-4-nonenoic acid, 7-methyloctanoic acid, 2-ethylheptanoic acid, (E)-4-nonenoic acid, 7-methylnonanoic acid, 2-ethylheptanoic acid, 2- or 8-methylnonanoic acid, Z- or E-3-undecenoic acid, undecanoic acid, dodecanoic acid, dodecanoic acid, tetradecanoic acid, hexadecanoic acid, and octadecanoic acid.

An ester such as ethyl formate, isoamyl formate, hexyl formate, (Z)-3-hexenyl formate, (E)-2-hexenyl formate, phenylethyl formate, geranyl formate, methyl acetate, ethyl acetate, butyl acetate, isobutyl acetate, 3-methylbutyl acetate, (Z)- or (E)-3-hexenyl acetate, (E)-2-hexenyl acetate, hexyl acetate, phenyl acetate, phenylethyl acetate, phenylethyl phenylacetate, benzyl acetate, geranyl acetate, α-terpinyl acetate, neryl acetate, linalyl acetate, bornyl acetate, (Z)- or (E)-3-hexenyl propionate, (E)-hexenyl propionate, neryl propionate, methyl butyrate, (Z)-3-hexenyl butyrate, (E)-2-hexenyl butyrate, benzyl butyrate, phenylethyl butyrate, phenylethyl isobutyrate, hexyl butyrate, (Z)-3-hexenyl 2-methylbutyrate, ethyl-3-hydroxybutyrate, methyl pentanoate, ethyl pentanoate, isobutyl pentanoate, (Z)-3-hexenyl pentanoate, (Z)- or (E)-2-pentenyl hexanoate, (E)-2-hexenyl hexanoate, (Z)-3-hexenyl hexanoate, phenylethyl hexanoate, hexyl hexanoate, (Z)-3-methylhexenoate, (E)-2-methylhexenoate, (Z)-3-hexenyl (E)-2-hexenoate, (E)-3-hexenyl (Z)-3-hexenoate, ethyl octanoate, hexyl octanoate, (Z)-3-hexenyl octanoate, ethyl decanoate, propyl decanoate, hexyl decanoate, (Z)-3-hexenyl decanoate, methyl phenylacetate, ethyl phenylacetate, hexyl phenylacetate, ethyl benzoate, hexyl benzoate, benzyl benzoate, (Z)-3-hexenyl benzoate, methyl 2-methoxybenzoate, methyl 4-methoxybenzoate, methyl jasmonate, methyl epijasmonate, methyl (Z)-dihydrojasmonate, neryl methyl propanoate, 1-hydroxy-2-propanone acetate, methyl succinate, methyl pentanoate, methyl octanoate, methyl 4-oxononanoate, 2-hexyl butyrate, methyl tetradecanoate, methyl pentadecanoate, ethyl pentadecanoate, methyl 11-hexadecenoate, methyl hexadecanoate, ethyl hexadecanoate, and methyl benzoate; a lactone such as δ-hexalactone, δ-heptalactone, δ-nonalactone, δ-decalactone, γ-butyrolactone, γ-valerolactone, γ-heptalactone, γ-hexalactone, γ-octalactone, γ-nonalactone, 2-methyl-γ-butyrolactone, 2-hexen-4-olide, 4-methyl-5-hexen-4-olide, 5-octene-4-olide, 2-nonene-4-olide, 7-decene-4-olide, loliolide, 2-methylbutanolide, γ-pentalactone, 5-octalactone, 3,7-decadiene-5-olide, cis-jasmine lactone, γ-decalactone, dihydroactinidiolide, bovolide, dihydrobovolide, and 4-tetradecanolide; a nitrogen-containing compound such as methylamine, ethylamine, diphenylamine, 1-ethylpyrrole, 2-formylpyrrole, 1-ethyl-2-formylpyrrole, 2-acetylpyrrole, 2-acetyl-1-ethylpyrrole, indole, 3-methylindole, pyrazine, methylpyrazine, ethylpyrazine, 2,3-dimethylpyrazine, 2,5-dimethylpyrazine, 2,6-dimethylpyrazine, 2-ethyl-3-methylpyrazine, 2-ethyl-5-methylpyrazine, 2-ethyl-6-methylpyrazine, 2-(2'-furyl)-5- or 2-(2'-furyl)-6-methylpyrazine, 2,5-diethylpyrazine, 2,6-diethylpyrazine, trimethylpyrazine, 3-ethyl-2,5-dimethylpyrazine, 2-ethyl-3,5-dimethylpyrazine, 2,5-diethyl-3-methylpyrazine, 2,3-diethyl-5-methylpyrazine, 3,5-diethyl-2-methylpyrazine, tetramethylpyrazine, 6,7-dihydro-5H-cyclopentapyrazine, 6,7-dihydro-2-methyl-5H-cyclopentapyrazine, 6,7-dihydro-5H-cyclopentapyrazine, 2-(2'-furyl)pyrazine, 2-methylpyridine, acetylpyridine, 3-methoxypyridine, 3-methylbutanenitrile, phenylnitrile, quinoline, 2-methylquinoline, 6- or 7-methylquinoline, 2,4-dimethylquinoline, 2,6-dimethylquinoline, 4,8-dimethylquinoline, diphenylamine, 3-propylquinoline, 2,6-dimethylpyridine, pyrrole, 1-methyl-2-formylpyrrole, 1-acetylpyrrole, 2,5-dimethylpyrrole, 1-methyl-2-acetylpyrrole, 1-methyl-propionylpyrrole, 2-acetyl-3-furfurylpyrrole, pyridine, 3- or 4-methylpyridine, 4-vinylpyridine, 2- or 3-ethylpyridine, 2,5-dimethylpyridine, 2-ethyl-6-methylpyridine, 5-ethyl-2-methylpyridine, propylpyrazine, 2,6-diethylpyrazine, and 2,4,5-trimethyloxazole.

A sulfur-containing compound such as methyl mercaptan, ethanethiol, 1-propanethiol, dimethyl sulfide, thiophene, tetrahydrothiophene, 2-methylthiophene, 3-methylthiophene, 3-methylthiophene-2-aldehyde, benzothiazole, 2-propionylthiophene, bis(2-methyl-3-furyl)disulfide, 4-metoxy-2-methyl-2-butanethiol, and 4-mercapto-2-pentanone; a phenol such as o-cresol, m-cresol, p-cresol, ethylphenol, 4-vinylphenol, 2,3-dimethylphenol, thymol, 1,3-di-tert-butyl-2-methoxy-5-methylbenzene, anethole, guaiacol, 4-ethylguaiacol, 1,4-dimethoxybenzene, diphenylether, safrole, eugenol, and carvacrol; a furan and a pyran such as linalool oxide (a five-membered ring in the E isomer or Z isomer and a six-membered ring in the E isomer or Z isomer), 2-ethylfuran, 2-pentylfuran, 2,3-dihydrofuran, furfural, 5-methylfurfural, sotolon, furaneol, 3,4-dimethyl-5-pentyl-2(5H)-furanone, 3,4-dimethyl-5-pentylidene-2(5H)-furanone, 2-acetylfuran, coumarin, maltol, ethyl maltol, theaspirone, (Z)- or (E)-theaspirone, (E)-theaspirane, (E)-6,7-epoxydihydrotheaspirane, (E)-6-hydroxydihydrotheaspirane, and furfuryl alcohol; natural perfume such as mace, violet, cassie, geranium, nutmeg, davana, jasmine, melilotus, green tea, black tea, oolong tea, barley tea, common sage, hay, oakmoss, osmanthus, coriander, cumin, thyme, allspice, bay laurel, birch, cardamom, celery, clove, dill, ginger, fenugreek, parsley, oregano, origanum, wintergreen, ylang-ylang, avocado, alfalfa, and palmarosa; jasmine absolute, rose absolute, tuberose absolute, vanilla absolute, and the like; and essential oil such as sandalwood oil, cedarwood oil, orange oil, chamomile oil, roman chamomile oil, cardamom oil, clary sage oil, grapefruit oil, clove oil, cinnamon oil, coriander oil, cypress oil, juniper berry oil, spearmint oil, and sage oil. Note that the above perfume components may be used singly or in combination of two or more kinds thereof.

Further, other additives are not particularly limited, and a known additive can be used. Examples thereof include a solvent such as water and ethanol; and a perfume retaining agent such as ethylene glycol, propylene glycol, dipropylene glycol, glycerol, hexyl glycol, benzyl benzoate, triethyl citrate, diethyl phthalate, hercolyn, a medium-chain fatty acid triglyceride, and a medium-chain fatty acid diglyceride. Note that the above additives may be used singly or in combination of two or more kinds thereof.

In the perfume (aroma) composition according to the present embodiment, a content of the pyrrole compound represented by the above formula (1) is not particularly limited and varies depending on the purpose, the kind of food and drink, cosmetics, and the like in which the aroma composition is used, and the kind of the aroma composition. However, for example, the content of the pyrrole compound is preferably from 10 mass ppt to 5 mass ppm (ppm by weight), more preferably from 50 mass ppt to 1 mass ppm (ppm by weight), particularly preferably from 0.1 mass ppb to 100 mass ppb (ppb by weight), with respect to the total mass of the aroma composition. Keeping the content of the pyrrole compound to 10 mass ppt or more can sufficiently impart metallic fragrance (odor) contributing to savory roasting flavor. On the other hand, keeping the content of the pyrrole compound to 5 mass ppm (ppm by weight) or less can prevent imparting of excessive fragrance and flavor properties (prevent imparting of fragrance and flavor properties as unpleasant smell), thus making it possible to impart fragrance excellent in natural feeling without causing too strong roasting aroma. Note that, when the aroma composition includes two or more kinds of the above pyrrole compounds, the total content of the pyrrole compounds is preferably with in the above range.

[Food and Drink]

In still another embodiment of the present invention, food and drink including the compound represented by the above formula (1) or the above aroma composition are provided. Note that the above pyrrole compound included in the food and drink may be used singly or by mixing two or more kinds thereof. The pyrrole compound and the aroma composition according to the present invention significantly contribute to roasting aroma, thus a deep rich savory flavor and a rich savory taste are imparted to or enhanced in the food and drink including them. Further, the pyrrole compound and the aroma composition according to the present invention has aroma with natural feeling. Thus, the food and drink including the pyrrole compound or the aroma composition are imparted with excellent roasting aroma with more of natural feeling.

Therefore, according to a still another embodiment of the present invention, there is provided a method for imparting roasting aroma to a food and drink, including a step of adding the compound or the aroma composition represented by the formula (1) above to the food and drink.

The food and drink according to the present embodiment are not particularly limited. However, they are preferably food and drink required to have savory flavor. Examples thereof include drink such as a tea beverage such as green tea (Sencha, Hojicha, Genmaicha, etc.), black tea, oolong tea, barley tea, and grain tea (corn tea, etc.), coffee (including a so-called coffee substitute prepared by roasting a dandelion root, a cherry tree root, burdock, etc.), beer, low-malt beer, quasi-beer, a low-malt beer-like beverage, and a non-alcohol beer-like beverage; and food such as a general food product including a processed meat product such as ham, sausage, and bacon, a processed seafood product such as a fish cake, meat and fish smoked products, confectionery such as a cookie, a pie, and a snack, a dairy produce such as cheese and butter, a nut such as almond and pistachio, a bean and the like, various instant food products, and the like. The above food and drink including the pyrrole compound or the aroma composition according to the present invention can be produced by adding the pyrrole compound or the aroma composition to the food and drink, followed by stirring, using a method known to those skilled in the art.

Of these, the preferable embodiment of the food and drink according to the present invention is a tea beverage. The tea beverage is not particularly limited, and examples thereof include tea prepared by processing a leave or a stem of the tea plant, which is an evergreen tree of the family Theaceae, a so-called tea substitute prepared by processing a plant other than the tea plant (specifically, a leaf, a stem, a fruit, a petal, etc. of the plant), and the like.

Examples of such a tea beverage include green tea (common Sencha, deep-steamed Sencha, Gyokuro, Kabusecha, Bancha, Tamaryokucha, Macha, Hojicha, Genmaicha, Mecha, Kukicha, etc.), black tea, oolong tea, barley tea, adlay tea, Pu'er tea, Rooibos tea, Mate tea, Kumazasa tea, bamboo leaf tea, buckwheat tea, senna tea, Ten-cha, Amacha, Amachazurucha, Eeucommia leaf tea, Kuding tea, Dokudami tea, Shiso tea, silver vine tea, honey citron tea, citrus peel tea (mandarin peel tea), ginger tea, vegetable tea such as ginseng tea, cinnamon tea, Sakura tea, Kombucha, Ume kombucha, mushroom tea such as Shiitake tea, corn tea, herbal tea, Kampo tea, Mamecha, and the like. Further, two or more kinds of the above teas may be mixed to prepare blend tea. Of these, the tea beverage of which roasting aroma has influence on the preference is particularly preferable. Specifically, Bancha, Hojicha, Genmaicha, oolong tea, barley tea, adlay tea, or blend tea including at least one selected therefrom is preferable.

Further, the extent of fermentation of tea is not particularly limited. For example, the tea may be any of green tea (non-fermented tea), white tea (lightly-fermented tea), blue tea (semi-fermented tea), black tea (completely fermented tea or fully fermented tea), yellow tea (post-heating lightly-fermented tea), black colored tea (post-heating fermented tea), and the like. Further, the above tea may or may not be roasted. Further, in the roasted tea, the extent of roasting is not specifically determined.

In the food and drink according to the present embodiment, a content of the pyrrole compound represented by the above formula (1) is not particularly limited and varies depending on the purpose, the kind of food and drink. However, for example, the content of the pyrrole compound is preferably from 0.01 mass ppt (10 mass ppq) to 1000 mass ppb (ppb by weight), more preferably from 0.05 mass ppt (50 mass ppq) to 100 mass ppb (ppb by weight), particularly preferably from 0.1 mass ppt to 50 mass ppb, and most preferably from 10 mass ppt to 10 mass ppb (ppb by weight)

with respect to the total mass of the food and drink. Keeping the content of the pyrrole compound to 0.01 mass ppt or more can provide food and drink having savory roasting aroma. On the other hand, keeping the content of the pyrrole compound to 1000 mass ppb or less can prevent imparting of excessive fragrance and flavor properties (prevent imparting of fragrance and flavor properties as unpleasant smell), thus making it possible to provide food and drink having fragrance excellent in natural feeling without causing too strong roasting fragrance. Note that, when the food and drink include two or more kinds of the above pyrrole compounds, the total content of the pyrrole compounds is preferably with in the above range.

A method for adding the compound represented by the above formula (1) or the above aroma composition to the food and drink is not particularly limited. The compound represented by the above formula (1) or the above aroma composition may be added at the same time or separately, or stepwise or continuously, to the food and drink. Further, a mixing method is not particularly limited, and a known mixing method can be used.

[Cosmetics]

In still another embodiment of the present invention, cosmetics including the compound represented by the above formula (1) or the above aroma composition are provided. Note that the above pyrrole compound included in the cosmetics may be used singly or by mixing two or more kinds thereof. Because the pyrrole compound and the aroma composition according to the present invention has fragrance with natural feeling, the food and drink including the pyrrole compound or the aroma composition are imparted with excellent roasting aroma with more of natural feeling.

The cosmetics according to the present embodiment is not particularly limited. However, the cosmetics is preferably cosmetics required to have roasting aroma with natural feeling. Example thereof include perfume; a hair care product such as shampoo, rinse, a hairdressing product (hair cream, pomade, etc.); a cosmetic such as foundation, a lipstick, lip cream, lip gloss, a skin lotion, a cosmetic emulsion, cosmetic cream, cosmetic gel, serum, and a pack agent; a suntan cosmetic such as a suntan product and a sunscreen product; a detergent for health and sanitation such as a face soap, a body soap, a laundry soap, a laundry detergent, a disinfectant detergent, and a deodorant detergent; a health and hygienic product such as a dentifrice, a tissue paper, and a toilet paper; and a fragrant product such as an indoor air refresher and car cologne.

Further, the form (formulation) of the cosmetics is not particularly limited. For examples, the cosmetics can be applicable to various forms such as liquid, emulsion, cream, paste, solid, and multilayer forms. In addition to those, the cosmetics can be applicable to a sheet preparation, a spray preparation, and a mousse preparation.

Such cosmetics including the pyrrole compound or the aroma composition according to the present invention can be produced by adding the pyrrole compound or the aroma composition to the cosmetics, followed by stirring, using a method known to those skilled in the art.

The cosmetics according to the present invention may include other additives as long as the desired fragrance is not impaired for the purpose of uniformly dispersing the pyrrole compound or the aroma composition according to the present invention at a proper concentration.

Other additives are not particularly limited, and a known additive can be used. Examples thereof include a hydrocarbon such as squalane, vaseline, and microcrystalline wax; an ester such as jojoba oil, carnauba wax, octyldodecyl oleate, phenylethyl acetate, phenylethyl butyrate, phenylethyl formate, phenethyl phenylacetate, phenylethyl isobutyrate, benzyl benzoate, phenylethyl propionate, and phenylpropyl acetate; an aldehyde such as phenylacetaldehyde, benzaldehyde, cinnamaldehyde, and hexyl cinnamaldehyde; a triglyceride such as olive oil, tallow, and coconut oil; a fatty acid such as stearic acid, oleic acid, ricinoleic acid; an alcohol such as linalool, citronellol, bacdanol, dihydromyrcenol, dihydrolinalool, geraniol, nerol, sandalore, santalex, terpineol, tetrahydrolinalool, benzyl alcohol, phenylethyl alcohol, phenylethyldimethylcarbinol, and hydroxycitronellal; a higher alcohol such as oleyl alcohol, stearyl alcohol, and octyldodecanol; a polyhydric alcohol such as ethylene glycol, propylene glycol, glycerol, and 1,3-butanediol; a nitrogen- and/or sulfur-containing compound such as indole, 5-methyl-3-heptanone oxime, limonenethiol, 1-p-menthene-8-thiol, butyl anthranilate, cis-3-hexenyl anthranilate, phenylethyl anthranilate, cinnamyl anthranilate, dimethyl sulfide, and 8-mercaptomenthone; an anionic surfactant such as sulfosuccinic acid ester and sodium polyoxyethylene alkyl sulfate; an ampholytic surfactant such as an alkyl betaine salt; a cationic surfactant such as a dialkylammonium salt; a nonionic surfactant such as a sorbitan fatty acid ester, a fatty acid monoglyceride, a polyoxyethylene adduct thereof, a polyoxyethylene alkyl ether, and a polyoxyethylene fatty acid ester; a thickening and gelling agent; an antioxidant; an ultraviolet light absorbent; a colorant; an antiseptic agent; a powder; and the like. Further, in addition to these, the other aroma components described in the above section [Aroma composition] can also be used as other additives in the cosmetics. Note that the above additives may be used singly or in combination of two or more kinds thereof.

In the cosmetics according to the present embodiment, a content of the pyrrole compound represented by the above formula (1) is not particularly limited and varies depending on the purpose, the kind of cosmetics. However, for example, the content of the pyrrole compound is preferably from 0.1 mass ppt to 100 mass ppb (ppb by weight), more preferably from 1 mass ppt to 10 mass ppb (ppb by weight), particularly preferably from 10 mass ppt to 5 mass ppb (ppb by weight) with respect to the total mass of the cosmetics. Keeping the content of the pyrrole compound to 0.1 mass ppt or more can provide the cosmetics having roasting aroma. On the other hand, keeping the content of the pyrrole compound to 100 mass ppb or less can prevent imparting of excessive fragrance and flavor properties (prevent imparting of fragrance and flavor properties as unpleasant smell), thus making it possible to provide cosmetics having fragrance excellent in natural feeling without causing too strong roasting aroma. Note that, when the cosmetics includes two or more kinds of the above pyrrole compounds, the total content of the pyrrole compounds is preferably with in the above range.

EXAMPLES

Hereinafter, the present invention will be described in further detail by way of Examples and Comparative examples. However, it should be noted that the present invention is not limited to the following Examples. Further, unless otherwise specified, each operation was performed under conditions of room temperature (25° C.) and relative humidity of from 40 to 50% RH. In the following description, unless otherwise specified, "ppt" and "ppb" refer to "mass ppt" and "mass ppb" (ppb by weight), respectively.

Note that, in the following description, the nuclear magnetic resonance spectrum ($^1$H-NMR) was measured using ECX-400A, 400 MHz manufactured by JEOL RESONANCE Co. Ltd. Further, the mass spectrum (MS) was measured using GC7890B, MS5977A (ionization method: EI 70 eV) manufactured by Agilent Technologies, Inc. Further, as a GC measurement column, TC-1 (length 30 m, inner diameter 0.25 mm, liquid layer thickness 0.25 micrometers) manufactured by GL Sciences Inc. was used.

Synthetic Example 1: Synthesis of Compounds (A), (B) and (D)

Synthesis of 1-hydroxymethyl pyrrole (Compound (i))

First, 1-hydroxymethyl pyrrole (compound (i)) was prepared in accordance with the following reaction formula (1) by referring to a method described in U.S. Pat. No. 2,492,414.

[Chemical Formula 7]

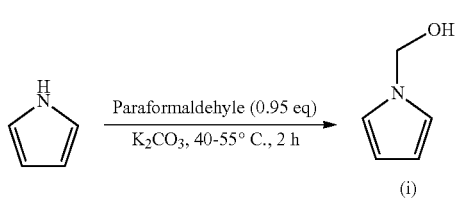

Reaction formula (1)

To 6.71 g (0.1 mol) of pyrrole, 2.85 g (0.095 mol) of paraformaldehyde and 0.02 g (0.00014 mol) of $K_2CO_3$ as a catalyst were added, and the resulting mixture was heated to 50° C. After the paraformaldehyde crystal was completely dissolved, the mixture was stirred for 2 hours while being kept at 40 to 55° C. The reaction solution was confirmed by GC-MS (TC-1) to find that the solution was a mixture of pyrrole as the raw material compound and 1-hydroxymethyl pyrrole as the objective compound, as well as 2-hydroxymethyl pyrrole and 2,5-dihydroxymethyl pyrrole. Thus, 1-hydroxymethyl pyrrole as the objective compound was purified by a silica gel column. Specifically, the following purification processing was performed.

The purification was performed using 150 g of WAKO gel C-100 and hexane/ethyl acetate as an eluent. Fractionation was performed while the mixing ratio of hexane/ethyl acetate was changed to obtain 5.99 g of 1-hydroxymethyl pyrrole. The resulting compound was confirmed by MS;

Compound (i): MS(EI) m/z: 97(100), 67(52)

Synthesis of compounds (A), (B) and (D)

Next, compounds (A), (B) and (D) were synthesized in accordance with the following reaction formula (2).

[Chemical Formula 8]

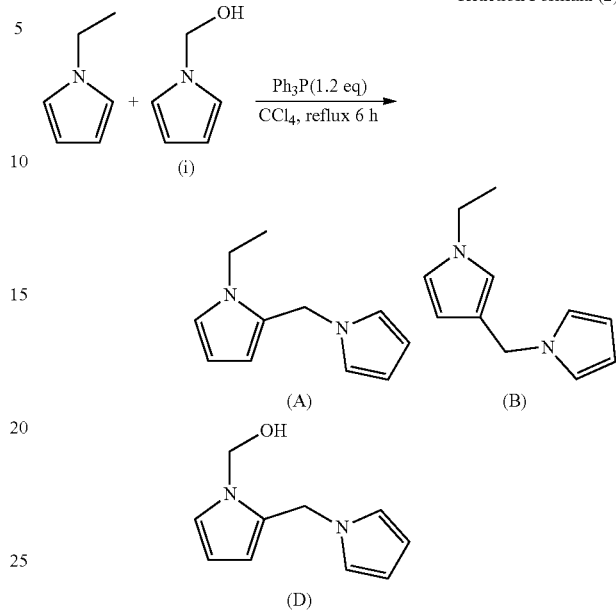

Reaction Formula (2)

Triphenylphosphine ($Ph_3P$) in an amount of 0.315 g (0.0012 mol) was dissolved in 5 mL of $CCl_4$. Next, a solution obtained by dissolving 0.1 g (0.001 mol) of 1-ethylpyrrole and 0.1 g (0.001 mol) of 1-hydroxymethyl pyrrole in 5 mL of $CCl_4$ was gradually added dropwise to the above solution under room temperature, and the resulting mixture was heated under reflux for 6 hours to simultaneously perform the Appel reaction and an addition reaction. The reaction mixture thus obtained was analyzed by GC-MS (TC-1) to confirm the termination of the reaction. Subsequently, purification was performed using a silica gel column. Specifically, the following purification processing was performed.

The purification was performed using 3 g of WAKO gel C-100 and hexane/ethyl acetate=99/1 (v/v) as an eluent. The effluent was fractionated to obtain a compound (A) (1-ethyl-2-(1-pyrrolylmethyl) pyrrole), a compound (B) (1-ethyl-3-(1-pyrrolylmethyl) pyrrole), and a compound (D) (1-hydroxymethyl-2-(1-pyrrolylmethyl) pyrrole).

Results of MS and NMR of the compounds thus obtained are shown below;

Compound (A): MS(EI) m/z: 108(100), 174(20), 80(18), 53(7). $^1$H-NMR (CDCl$_3$, 400 MHz) δ (ppm) 1.13 (3H, t, J=7.2 Hz), 3.73 (2H, q, J=7.2 Hz), 5.02 (2H, s), approximately 6.12 (1H, m), 6.13 (2H, dd, J=2.4, 1.6 Hz), 6.17 (1H, dd, J=3.2, 1.6 Hz), 6.62 (2H, dd, J=2.4, 1.6 Hz), 6.69 (1H, m).

Compound (B): MS(EI) m/z: 108(100), 174(33), 80(17), 53(7).

Compound (D): MS(EI) m/z: 80(100), 176(21), 81(20), 53(13).

Further, the fragrance note of the above compounds (A), (B), and (D) was confirmed to find that all compounds had savory roasting aroma.

Synthetic Example 2: Synthesis of Compound (C)

Synthesis of 1-ethyl-2-formylpyrrole (Compound (ii))

First, 1-ethyl-2-formylpyrrole (compound (ii)) was prepared in accordance with the following reaction formula (3).

[Chemical Formula 9]

Reaction formula (3)

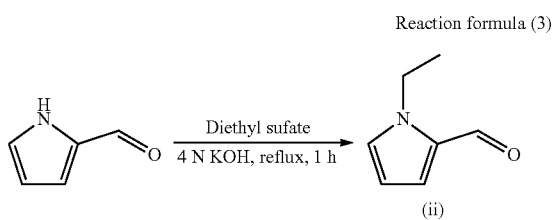

In a 1 L four-necked flask, 19 g (0.2 mol) of pyrrole-2-carboxaldehyde and 50 mL of 4N KOH were placed, followed by heating at 100° C. in an oil bath. To this, 92.4 g (0.6 mol) of diethyl sulfate and 175 mL of 4N KOH were added dropwise through different ports over about 1 hour with stirring. After the dropwise addition was completed, the mixture was refluxed for another 1 hour with stirring (by referring to the description of U.S. Pat. No. 3,403,159). After confirming the production of a black precipitate, the mixture was cooled after refluxing. To the mixture, 300 mL of diethyl ether was added, and the resulting mixture was sufficiently stirred. After filtration with a Nutsche filter, the filtrate was separated using a separatory funnel. The organic layer was washed with 100 mL of 2N KOH and 100 mL of ultrapure water. After dehydration over anhydrous sodium sulfate, diethyl ether was removed using an evaporator to obtain a black oily matter. The black oily matter was purified by a silica gel column. Specifically, the following purification processing was performed.

The black oily matter was charged into a column prepared by using 300 g of WAKO gel C-100, and then hexane was allowed to pass through the column. Subsequently, having hexane/ethyl acetate=95/5 (v/v) passed through the column, the effluent was fractionated to obtain 11.6 g of a compound (ii) as a yellow oily matter. The purity of the compound (ii) was 98.13%. The compound was confirmed by MS;

Compound (ii): MS(EI) m/z: 123(100), 94(65), 122(32), 108(30), 106(23), 80(15), 66(15), 39(15).

Synthesis of 1-ethyl-2-hydroxymethyl pyrrole (Compound (iii))

Next, 1-ethyl-2-hydroxymethyl pyrrole (compound (iii)) was prepared in accordance with the following reaction formula (4).

[Chemical Formula 10]

Reaction formula (4)

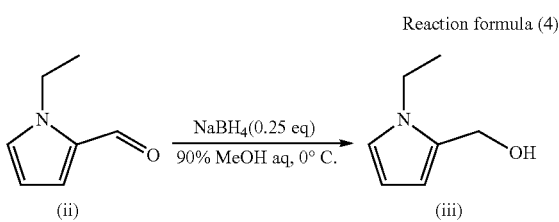

Under ice cooling with stirring, 0.0756 g (0.002 mol) of $NaBH_4$ was gradually added to 1.0 g (0.008 mol) of the above compound (ii), 9 mL of methanol, and 1 mL of ultrapure water. The reaction was continued while being monitored by GC-MS (TC-1). After further adding 0.0189 g (0.0005 mol) of $NaBH_4$ to the mixture, the mixture was stirred overnight. Subsequently, 10 mL of a saturated salt solution was added, and a liquid-separating operation was performed twice using 20 mL of diethyl ether. The organic layer was washed with the equal amount of a saturated salt solution and dehydrated over anhydrous sodium sulfate. Then, diethyl ether was removed using an evaporator to obtain 1.18 g of a compound (iii). The compound was confirmed by MS; Compound (iii): MS(EI) m/z: 108(100), 125(74), 80(43), 68(20).

Synthesis of Compound (C)

Further, compound (C) was synthesized in accordance with the following reaction formula (5).

[Chemical Formula 11]

Reaction formula (5)

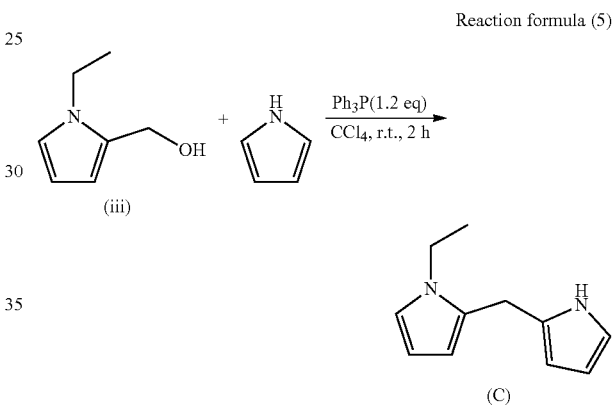

Triphenylphosphine ($Ph_3P$) in an amount of 0.26 g (0.001 mol) was dissolved in 2 mL of $CCl_4$. Next, to this solution, a mixture of 0.10 g (0.0008 mol) of the above compound (iii) and 0.067 g (0.001 mol) of pyrrole dissolved in 8 mL of $CCl_4$ was gradually added dropwise, followed by stirring at room temperature. After the reaction was continued for 2 hours, purification was performed using a silica gel column. Specifically, the following purification processing was performed.

The purification was performed using 3 g of WAKO gel C-100 and hexane/ethyl acetate as an eluent. The sample was charged into a column and then hexane was allowed to pass through the column. Subsequently, having hexane/ethyl acetate=95/5 (v/v) passed through the column, the effluent was fractionated to obtain 26.4 mg of a compound (C) (1-ethyl-2-(2-pyrrolylmethyl) pyrrole) as a brown oily matter. The purity of the compound (C) was 94.75%.

Results of MS and NMR of the compounds thus obtained are shown below;

Compound (C): MS(EI) m/z: 174(100), 173(57), 95(37), 80(32), 145(19).

$^1$H-NMR ($CDCl_3$, 400 MHz) δ (ppm) 1.18 (3H, t, J=7.2 Hz), 3.77 (2H, q, J=7.2 Hz), 3.96 (2H, s), 5.99 (2H, m), approximately 6.12 (2H, m), 6.64 (2H, m), 7.87 (1H, br).

Further, the fragrance note (odor) of the above compound (C) was confirmed to find that the compounds had savory roasting aroma.

Example 1: Addition to Hojicha

The compound (A) obtained in the above Synthetic example 1 was added to commercially available Hojicha at a concentration described in Table 1 below, and evaluation was made by twenty expert panelists. Further, evaluation was made in the same manner using 2-methylpyrazine (Comparative example 1-2). Evaluation criteria are as follows (the same hereinafter);

(Evaluation Criteria)
−: No significant difference from control.
+: Roasting aroma with natural feeling is slightly sensed.
++: Roasting aroma with natural feeling is sensed.
+++: Remarkable roasting aroma excellent in natural feeling is sensed.

TABLE 1

| Hojicha | Concentration of compound (A) | Evaluation | Evaluation of aroma and taste |
|---|---|---|---|
| Comparative Example 1-1 (Control) | (No additive) | − | |
| Comparative Example 1-2 | (2-methylpyrazine 200 ppb) | − | |
| Reference Example 1-1 | 1 ppt | − | |
| Example 1-1 | 10 ppt | ++ | Enhancing roasting aroma, savory taste, and sweet taste. |
| Example 1-2 | 100 ppt | +++ | Enhancing roasting aroma, savory taste, and sweet taste. Building complex flavor. |
| Example 1-3 | 1 ppb | +++ | Enhancing roasting aroma, savory taste, and sweet taste. Building complex flavor. |
| Example 1-4 | 10 ppb | +++ | Enhancing roasting aroma, savory taste, and sweet taste. Building complex flavor. Leaving strong aftertaste. |
| Example 1-5 | 100 ppb | ++ | Enhancing roasting aroma, savory taste, and sweet taste. Leaving very strong aftertaste. |

Example 2: Addition to Green Tea

The compound (A) obtained in the above Synthetic example 1 was added to commercially available green tea at a concentration described in Table 2 below, and evaluation was made in the same manner as in the above Example 1.

TABLE 2

| Green tea | Concentration of compound (A) | Evaluation | Evaluation of aroma and taste |
|---|---|---|---|
| Comparative Example 2-1 (Control) | (No additive) | − | |
| Reference Example 2-1 | 1 ppt | − | |
| Example 2-1 | 10 ppt | ++ | Enhancing roasting aroma |
| Example 2-2 | 100 ppt | +++ | Exhibiting roasting aroma, leaving aftertaste. |
| Example 2-3 | 1 ppb | + | Exhibiting slightly strong roasting aroma. |

Example 3: Addition to Coffee

The compound (A) obtained in the above Synthetic example 1 was added to commercially available coffee at a concentration described in Table 3 below, and evaluation was made in the same manner as in the above Example 1.

TABLE 3

| Coffee | Concentration of compound (A) | Evaluation | Evaluation of aroma and taste |
|---|---|---|---|
| Comparative Example 3-1 (Control) | (No additive) | − | |
| Reference Example 3-1 | 0.001 ppt | − | |
| Example 3-1 | 0.01 ppt | + | Enhancing aftertaste. |
| Example 3-2 | 0.1 ppt | + | Enhancing aftertaste. |
| Example 3-3 | 1 ppt | ++ | Enhancing sharp fragrance, roasting flavor, and aftertaste. |
| Example 3-4 | 10 ppt | +++ | Enhancing roasting flavor and charcoal fire flavor. |
| Example 3-5 | 100 ppt | +++ | Enhancing roasting flavor and charcoal fire flavor, leaving aftertaste. |
| Example 3-6 | 1000 ppt | ++ | Enhancing burnt flavor, leaving strong aftertaste. |

Example 4: Addition to Barley Tea

The compound (A) obtained in the above Synthetic example 1 was added to commercially available barley tea at a concentration described in Table 4 below, and evaluation was made in the same manner as in the above Example 1.

TABLE 4

| Barley tea | Concentration of compound (A) | Evaluation | Evaluation of aroma and taste |
|---|---|---|---|
| Comparative Example 4-1 (Control) | (No additive) | − | |
| Reference Example 4-1 | 1 ppt | − | |
| Example 4-1 | 10 ppt | + | Enhancing roasting aroma. |
| Example 4-2 | 100 ppt | ++ | Enhancing roasting aroma and sweet taste. |
| Example 4-3 | 1000 ppt | + | Enhancing roasting aroma. |

Example 5: Addition to Non-Alcohol Beer

The compound (A) obtained in the above Synthetic example 1 was added to commercially available non-alcohol beer at a concentration described in Table 5 below, and evaluation was made in the same manner as in the above Example 1.

TABLE 5

| Non-alcohol beer | Concentration of compound (A) | Evaluation | Evaluation of aroma and taste |
|---|---|---|---|
| Comparative Example 5-1 (Control) | (No additive) | − | |
| Example 5-1 | 1 ppt | + | Exhibiting sharp fragrance. |
| Example 5-2 | 10 ppt | ++ | Enhancing top note fragrance. |
| Example 5-3 | 100 ppt | +++ | Enhancing top note fragrance and depth in taste. |
| Example 5-4 | 1000 ppt | ++ | Enhancing top note fragrance and exhibiting slight roasting flavor. |

Example 6: Addition to Muguet Aroma Composition

Table 6 shows a prescription of a Muguet aroma composition. The compound (A) obtained in the above Synthetic example 1 was added to this prescription, and evaluation was made in the same manner as in the above Example 1. Note that a unit of each numerical value in Table 6 is "mass part" unless otherwise specified. Note that the Muguet aroma composition in Example 6-1 was obtained by adding the compound (A) to the Muguet aroma composition in Comparative example 6-1 at a concentration of 1 mass ppb.

TABLE 6

| Muguet aroma composition | Comparative Example 6-1 (Control) | Example 6-1 |
|---|---|---|
| Linalool | 30 | 30 |
| Citronellol | 150 | 150 |
| Phenethyl phenylacetate | 50 | 50 |
| Phenylethyl alcohol | 70 | 70 |
| Phenylethyldimethylcarbinol | 200 | 200 |
| Hydroxycitronellal | 250 | 250 |
| Indole 10% DPG | 20 | 20 |
| Hexyl cinnamaldehyde | 80 | 80 |
| Sandalwood oil | 50 | 50 |
| Phenylethyl isobutyrate | 20 | 20 |
| Jasmine absolute | 10 | 10 |
| Benzyl benzoate | 70 | 70 |
| Compound (A) | — | 1 ppb |

TABLE 7

| Muguet aroma composition | Concentration of compound (A) | Evaluation | Evaluation of fragrance |
|---|---|---|---|
| Comparative Example 6-1 (Control) | (No additive) | − | |
| Example 6-1 | 1 ppb | ++ | Enhancing top note fragrance and greenish note fragrance, improving fragrance-long lasting property. |

Results in the above Tables 1 to 5 and 7 showed that the pyrrole compound according to the present invention was highly effective in contributing to savory roasting flavor (contributing to aroma) and capable of imparting aroma with natural feeling to food and drink and cosmetics.

Further, the present application is based on the Japanese patent application No. 2017-144630 filed on Jul. 26, 2017, the entire contents of which is hereby incorporated by reference.

The invention claimed is:

1. A compound represented by a formula selected from the following formulae (B) to (E):

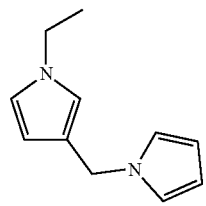
(B)

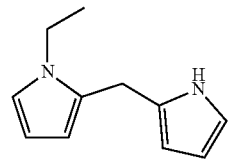
(C)

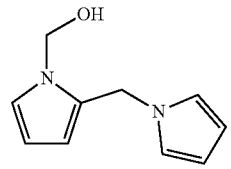
(D)

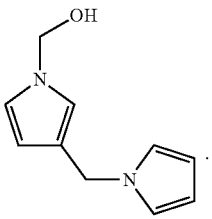
(E)

2. An aroma composition comprising a compound represented by the following formula (1) as an active ingredient:

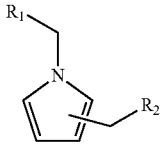
(1)

wherein, $R_1$ is a linear or branched alkyl group having 1 to 3 carbon atoms or a hydroxyl group; and $R_2$ is a 1-pyrrolyl group, a 2-pyrrolyl group, or a 3-pyrrolyl group, and a synthetic perfume or a perfume retaining agent.

3. A food or drink comprising a food or drink component and a compound represented by the following formula (1):

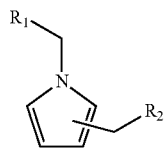

wherein, $R_1$ is a linear or branched alkyl group having 1 to 3 carbon atoms or a hydroxyl group; and $R_2$ is a 1-pyrrolyl group, a 2-pyrrolyl group, or a 3-pyrrolyl group, and
the content of the compound is 0.01 mass ppt to 1000 mass ppb relative to a total mass of the food or drink.

4. The food or drink according to claim 3, wherein the food or drink is a tea beverage.

5. A cosmetics comprising a compound represented by the following formula (1):

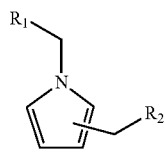

wherein, $R_1$ is a linear or branched alkyl group having 1 to 3 carbon atoms or a hydroxyl group; and $R_2$ is a 1-pyrrolyl group, a 2-pyrrolyl group, or a 3-pyrrolyl group, and
a content of the compound is 0.1 mass ppt to 100 mass ppb relative to the total mass of the cosmetics.

6. A method for imparting roasting aroma to a food or drink, comprising a step of adding a compound represented by the following formula (1) to the food or drink, wherein an added amount of the compound is 0.01 mass ppt to 1000 mass ppb relative to a total mass of the food or drink,

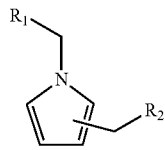

wherein, $R_1$ is a linear or branched alkyl group having 1 to 3 carbon atoms or a hydroxyl group; and $R_2$ is a 1-pyrrolyl group, a 2-pyrrolyl group, or a 3-pyrrolyl group.

7. A food and or drink comprising the aroma composition according to claim 2.

8. A cosmetics comprising the aroma composition according to claim 2.

9. A method for imparting roasting aroma to a food or drink, comprising a step of adding the aroma composition according to claim 2 to the food or drink.

10. The aroma composition according to claim 2, wherein a content of the compound is 10 mass ppt to 5 mass ppm relative to the total mass of the aroma composition.

11. The food or drink according to claim 7, wherein a content of the compound is 0.01 mass ppt to 1000 mass ppb relative to a total mass of the food or drink.

12. The cosmetics according to claim 8, wherein a content of the compound is 0.1 mass ppt to 100 mass ppb relative to a total mass of the cosmetics.

13. The method for imparting roasting aroma to a food or drink according to claim 9, wherein an added amount of the compound is 0.01 mass ppt to 1000 mass ppb relative to a total mass of the food or drink.

14. A method for producing a compound represented by the following formula (1):

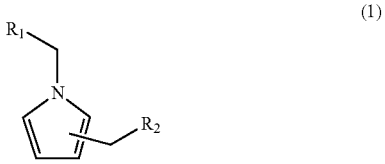

wherein, $R_1$ is a linear or branched alkyl group having 1 to 3 carbon atoms or a hydroxyl group; and $R_2$ is a 1-pyrrolyl group, a 2-pyrrolyl group, or a 3-pyrrolyl group, comprising:
performing Appel reaction and an addition reaction simultaneously using 1-alkylpyrrole and 1-hydroxymethyl pyrrole;
performing halogenation of a hydroxyl group of 1-hydroxymethyl pyrrole to obtain a halide, followed by performing a coupling reaction of the halide with 1-alkylpyrrole; or
performing a coupling reaction between 1-alkyl-2-hydroxymethyl pyrrole and pyrrole.

* * * * *